（12) United States Patent
Adler

(10) Patent No.: US 7,551,955 B2
(45) Date of Patent: Jun. 23, 2009

(54) DEVICE, SYSTEM AND METHOD FOR IMAGE BASED SIZE ANALYSIS

(75) Inventor: Doron Adler, Nesher (IL)

(73) Assignee: Given Imaging Ltd., Yoqneam (IL)

( * ) Notice: Subject to any disclaimer, the term of this patent is extended or adjusted under 35 U.S.C. 154(b) by 1003 days.

(21) Appl. No.: 10/402,245

(22) Filed: Mar. 31, 2003

(65) Prior Publication Data

US 2004/0258328 A1 Dec. 23, 2004

Related U.S. Application Data

(63) Continuation of application No. PCT/IL02/01025, filed on Dec. 19, 2002.

(30) Foreign Application Priority Data

Dec. 20, 2001 (IL) .................................. 147221

(51) Int. Cl.
A61B 5/05 (2006.01)
(52) U.S. Cl. .................. 600/424; 382/128; 600/476
(58) Field of Classification Search .............. 600/424, 600/407, 476, 473, 423, 117; 382/160, 286, 382/128, 916; 356/21; 358/98
See application file for complete search history.

(56) References Cited

U.S. PATENT DOCUMENTS

| 3,971,362 | A | 7/1976 | Pope et al. |
| 4,217,045 | A | 8/1980 | Ziskind |
| 4,278,077 | A | 7/1981 | Mizumoto |
| 4,431,005 | A | 2/1984 | McCormick |
| 4,651,201 | A | 3/1987 | Schoolman |
| 4,656,508 | A | 4/1987 | Yokota |
| 4,689,621 | A | 8/1987 | Kleinberg |
| 4,714,319 | A | 12/1987 | Zeevi et al. |
| 4,844,076 | A | 7/1989 | Lesho et al. |
| 4,881,032 | A | 11/1989 | Bottomley et al. |
| 4,895,431 | A | 1/1990 | Tsujiuchi et al. |
| 4,980,763 | A * | 12/1990 | Lia ............................ 348/67 |
| 5,279,607 | A | 1/1994 | Schentag et al. |

(Continued)

FOREIGN PATENT DOCUMENTS

DE 34 40 177 5/1986

(Continued)

OTHER PUBLICATIONS

The Radio Pill, Rowlands, et al., British Communications and Electronics, Aug. 1960, pp. 598-601.

(Continued)

Primary Examiner—Eric F Winakur
Assistant Examiner—Lawrence N Laryea
(74) Attorney, Agent, or Firm—Pearl Cohen Zedek Latzer, LLP

(57) ABSTRACT

A device, system and method for calculating a size of an object using images acquired by a typically moving imager, for example in the gastrointestinal (GI) tract. A distance traveled by the moving imager during image capture may be determined, and spatial coordinates of image pixels may be calculated using the distance. The size of the object may be determined, for example, from the spatial coordinates. The moving imager may be in a swallowable capsule, or, for example, an endoscope.

13 Claims, 5 Drawing Sheets

U.S. PATENT DOCUMENTS

| | | | |
|---|---|---|---|
| 5,575,754 | A | 11/1996 | Konomura |
| 5,604,531 | A | 2/1997 | Iddan et al. |
| 5,728,044 | A | 3/1998 | Shan |
| 5,819,736 | A | 10/1998 | Avny et al. |
| 5,833,603 | A | 11/1998 | Kovacs et al. |
| 5,853,005 | A | 12/1998 | Scanlon |
| 5,944,655 | A | 8/1999 | Becker |
| 5,967,968 | A * | 10/1999 | Nishioka .................... 600/117 |
| 6,009,189 | A | 12/1999 | Schaack |
| 6,074,349 | A | 6/2000 | Crowley |
| 6,165,128 | A | 12/2000 | Céspedes et al. |
| 6,240,312 | B1 | 5/2001 | Alfano et al. |
| 6,245,057 | B1 | 6/2001 | Sieben et al. |
| 6,289,232 | B1 | 9/2001 | Jakob et al. |
| 6,944,316 | B2 * | 9/2005 | Glukhovsky et al. ........ 382/107 |
| 6,950,690 | B1 * | 9/2005 | Meron et al. ................ 600/424 |
| 2001/0051766 | A1 | 12/2001 | Gazdzinski |
| 2002/0107444 | A1 * | 8/2002 | Adler ......................... 600/424 |
| 2002/0173718 | A1 * | 11/2002 | Frisch et al. ................ 600/424 |
| 2003/0139661 | A1 * | 7/2003 | Kimchy et al. .............. 600/407 |

FOREIGN PATENT DOCUMENTS

| | | |
|---|---|---|
| JP | 4109927 | 4/1992 |
| JP | 5015515 | 1/1993 |
| JP | 2001224553 | 8/2001 |
| WO | WO 01/08548 | 2/2001 |
| WO | WO 01/50941 | 7/2001 |
| WO | WO 01/65995 | 9/2001 |

OTHER PUBLICATIONS

Video Camera to "Take"—RF System Lab, Dec. 25, 2001.

Wellesley company sends body monitors into space—Crum, Apr. 1998.

Wireless transmission of a color television moving image from the stomach using a miniature CCD camera, light source and microwave transmitter. Swain CP, Gong F, Mills TN, Gastrointest Endosc 1997;45:AB40.

BBC News Online—Pill camera to 'broadcast from the gut', Feb 21, 2000, www.news.bbc.co.uk.

Machine Vision, Theory, Algorithms, Practicalities E.R. Davies, Academic Press 1996, pp. 441-444.

Robust shape reconstruction from combined shading and stereo information—Lee, et al., SPIE vol. 1771 Applications of Digital Image Processing XV (1992), pp. 171-182.

Shedding light on cancer diagnosis—Powell (Ed.), May 2000, Laser Focus World.

Simulation of images by photometric stereo modeling, Russell, et al., Optical Engineering, Sep. 1991, vol. 30, No. 9, pp. 1337-1345.

Two Image Photometric Stereo Method, Yang et al., SPIE vol. 1826, Intelligent Robots and Computer Vision XI (1992).

www.oceanoptics.com—pH Sensor & Accessories, © 2001.

* cited by examiner

DEVICE, SYSTEM AND METHOD FOR IMAGE BASED SIZE ANALYSIS

CROSS-REFERENCE TO RELATED APPLICATIONS

This application is a continuation application of PCT Patent Application No. PCT/IL02/01025, filed Dec. 19, 2002, which is hereby incorporated by reference. PCT Patent Application No. PCT/IL02/01025 filed Dec. 19, 2002, claims the benefit of Israeli Application No. 147221 filed Dec. 20, 2001.

FIELD OF THE INVENTION

The present invention relates to a method and system for size analysis based on images captured by a camera system.

BACKGROUND OF THE INVENTION

One of the most important ways a physician has for analyzing a pathological condition is to examine the dimensions of the pathological entity. In the digestive tract, including the intestines, determination of size of an object within the tract can provide important information useful in diagnosing a condition and prescribing treatment.

Prior art systems exist for measuring in vivo distances however, such prior art systems suffer from, inter alia, not being able to view or image certain areas of the gastrointestinal (GI) tract, being uncomfortable or difficult to use in some patients.

Therefore, there is a need for an easy to use size analysis system which can more extensively provide views of the GI tract.

SUMMARY OF THE INVENTION

There is provided, in accordance with one embodiment of the present invention, a device, system and method for calculating a size of an object using images acquired by a moving imager.

In one embodiment there is provided a device, system and method for calculating a size of an object in vivo, for example in the GI tract, using in vivo images acquired by a moving imager. In one embodiment, the moving imager includes a single camera. The imager may include more than one camera or imaging device. There is provided, in accordance with another embodiment of the present invention, a device, system and method for calculation of object size by conversion of two-dimensional images, where the two-dimensional images are acquired by a moving imager. The embodiment includes a distance-detecting unit for determining a distance traveled by the moving imager during the capture of two of the images, and at least one processor for generating spatial coordinates of objects within the images. The processor uses the distance obtained by the distance-detecting unit, and converts the spatial coordinates into a size calculation of the object.

In one embodiment, the distance-detecting unit uses data provided by a sensor. In one embodiment, the sensor is a position sensor which has three receivers which receive signals from a transmitter in communication with the camera system, the receiver in communication with a unit for determining the position of the camera system. The position sensor may be an induction coil. In another embodiment, the sensor is an imager providing data to an image analyzer which can analyze, for example, the optical flow of an image. In another embodiment, the sensor is a velocity sensor, which may be an accelerometer or an ultrasound transducer.

Certain functions and units, such as a distance detecting unit or a size calculation unit, may be completely or partially located externally to the capsule, for example in a display station or workstation.

According to one embodiment, a method for calculating a size of an object in vivo using images acquired by an imager device includes: determining a distance traveled by said imager during capture of two of said images; calculating relative spatial coordinates of a set of objects within said images using said distance; and calculating the size of one of the set of objects from said spatial coordinates. The distance traveled may be non-negligible as compared to a distance between said imager and said objects. In one embodiment, the moving imager is an in vivo imager. The method may include determining the position of the imager, determining the velocity of the imager, determining an optical flow of the images, determining the distance traveled by analyzing the images, and/or other calculation. The object may be in a gastrointestinal tract.

The imager may be within, for example, an endoscope, a swallowable capsule, or other device.

In one embodiment a system for calculation of object size using images acquired by an imager includes a sensor capable of providing data used for determining a distance traveled by said imager during the capture of two of said images; and at least one processor for generating spatial coordinates of objects within said images, said processor calculating a distance using data obtained by said sensor, wherein said at least one processor is capable of converting said spatial coordinates into a size calculation of an object.

In one embodiment a system for calculation of object size using images acquired by an in-vivo imager device includes: at least one processor capable of receiving data from a sensor, said processor capable of generating spatial coordinates of objects within said images and calculating a distance using data obtained by said sensor, wherein said at least one processor is capable of converting said spatial coordinates into a size calculation of said object. The sensor may be located in the imager device or, alternately, outside a patient's body. The sensor may include an accelerometer, an ultrasound transducer, a camera, a position sensor, an induction coil, and/or other equipment. The processor may include an image analyzer which is capable of analyzing the optical flow of an image and/or which is capable of determining a distance traveled by analyzing the images. The data obtained by said sensor may be capable of being used by said processor to calculate a velocity.

In one embodiment a swallowable capsule includes an image sensor capable of obtaining images from within the gastrointestinal tract; a distance-detecting sensor capable of generating data for determining a distance traveled by said capsule during reception of at least two of said images, wherein said data may be used by a processor for generating spatial coordinates of at least one object found within said two images and for converting said spatial coordinates into a size calculation of said at least one object. The sensor may include an accelerometer, an ultrasound transducer, a camera, a position sensor, an induction coil, and/or other equipment.

BRIEF DESCRIPTION OF THE DRAWINGS

The present invention will be understood and appreciated more fully from the following detailed description taken in conjunction with the drawings in which.

Similar elements in the Figures are numbered the same throughout.

DETAILED DESCRIPTION OF THE INVENTION

In the following detailed description, numerous specific details are set forth in order to provide a thorough understanding of the invention. However it will be understood by those of ordinary skill in the art that the present invention may be practiced without these specific details. In other instances, well-known methods and procedures have not been described in detail so as not to obscure the present invention.

An in vivo video camera system captures and transmits images of, for example, the GI tract while the capsule passes through the GI lumen. Some embodiments may be contained within a capsule; alternate configurations, such as within an endoscope, are possible. In addition to the camera system, embodiments contain an optical system for imaging an area of interest onto the camera system and a transmitter for transmitting image output of the camera. A capsule including such components can, for example, pass through the entire digestive tract and operate as an autonomous video endoscope. It may image difficult to reach areas of the small intestine. Embodiments of U.S. Pat. No. 5,604,531, assigned to the common assignee of the present application and incorporated herein by reference, describe an in vivo camera system, which is carried by a swallowable capsule. Another in-vivo imaging system is described in International Application Publication No WO01/65995 published Sep. 13, 2001, assigned to the common assignee of the present application and incorporated herein by reference. While embodiments of the system and method of the present invention may be used with devices and methods described in U.S. Pat. No. 5,604,531 and/or International Application Publication No WO01/65995, embodiments of the present invention may be used with other in-vivo imaging systems, having other configurations.

Figure 1:
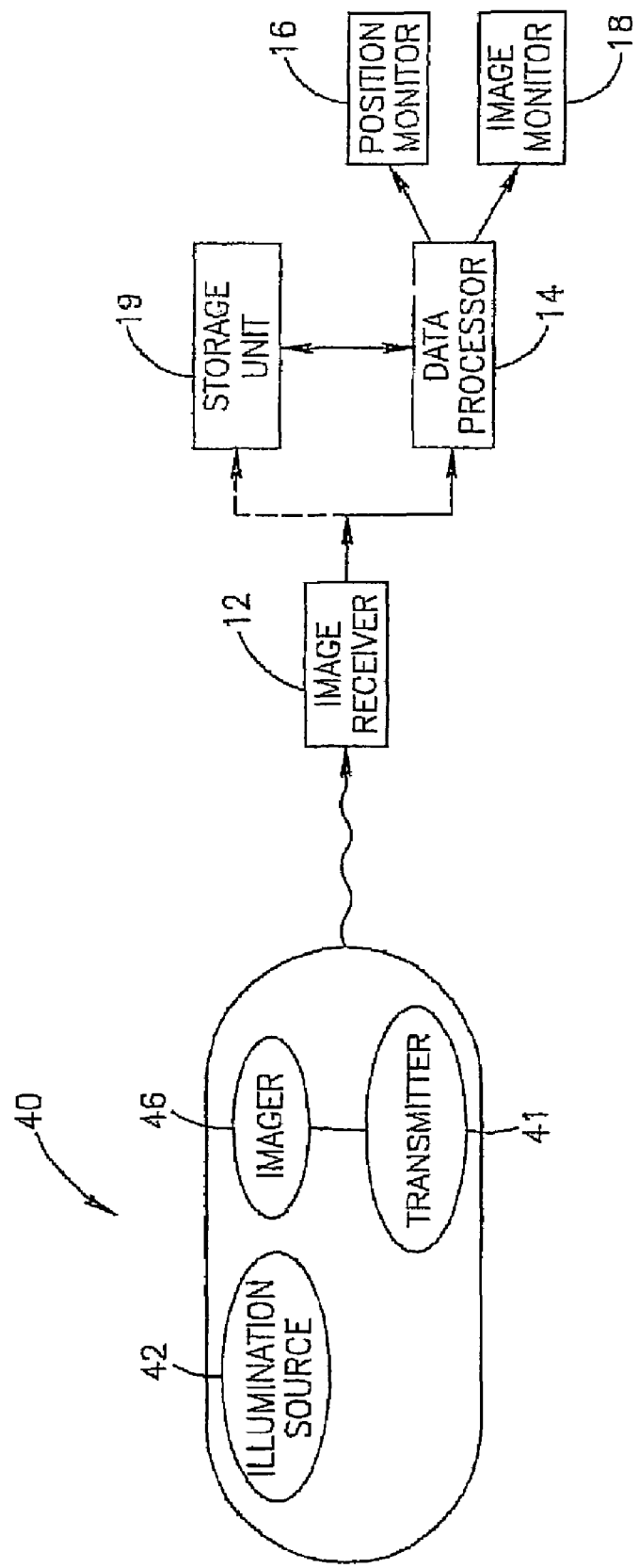
FIG. 1 is a schematic illustration of a prior art in vivo camera system.

Reference is made to FIG. 1, which shows a schematic diagram of an in-vivo imaging system. The system includes a capsule 40 having, for example, an imager 46, an illumination source 42, and a transmitter 41. Outside the patient's body are an image receiver 12 (for example an antenna array), a storage unit 19, a data processor 14, an image monitor 18, and a position monitor 16. While FIG. 1 shows separate monitors, both an image and its position can be presented on a single monitor.

Imager 46 in capsule 40 may be connected to transmitter 41 also located in capsule 40. Transmitter 41 transmits images to image receiver 12, which sends the data to, for example, a data processor 14 and a storage unit 19. Data processor 14 may, for example, analyze the data and may be in communication with storage unit 19, transferring frame data to and from storage unit 19. Data processor 14 also may provide the analyzed data to image monitor 18 and position monitor 16 where the physician views the data. The image monitor may present an image of the GI lumen and the position monitor may present the position in the GI tract at which the image was taken. The data can be viewed in real time or at some later date. In addition to revealing pathological conditions of the GI tract, the system can provide information about the location of these pathologies. The imaging device may include more than one camera or imaging device.

Embodiments of the present invention relate to a method, device and system of size analysis by converting two-dimensional images, captured by a moving in-vivo video camera system, such as that of FIG. 1, into three-dimensional representations. This conversion is typically done using only one camera or imager, and is typically based on the velocity of the camera system when it captures the frames being converted.

Embodiments of the present invention may be used with embodiments or modified embodiments of the image capture, reception and display system such as embodiments described in U.S. Pat. No. 5,604,531 and/or International Application Publication No WO01 65995 published Sep. 13, 2001.

Figure 2:
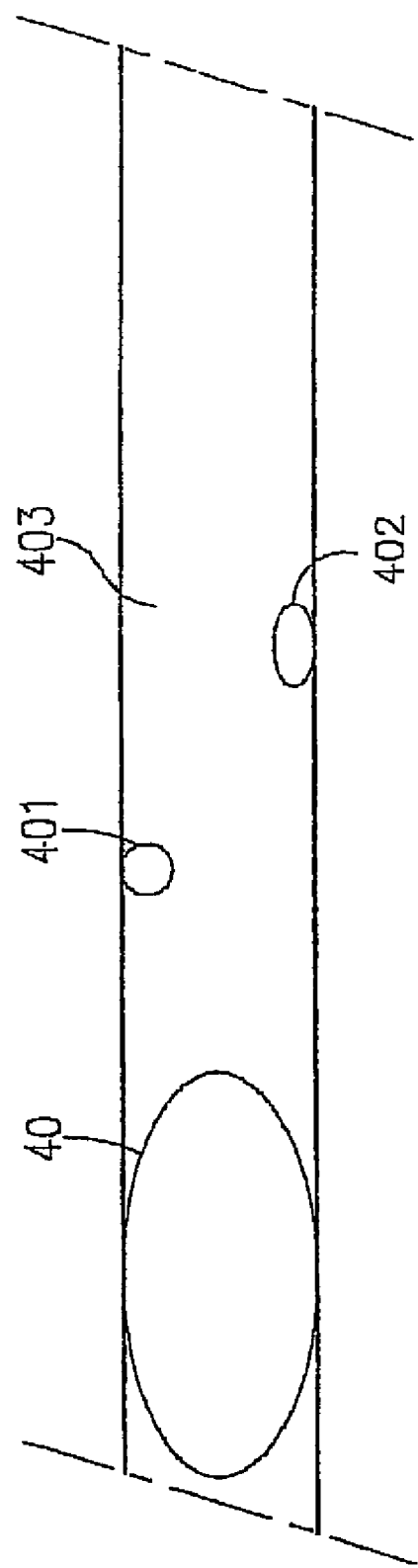
FIG. 2 is schematic illustration of an in vivo camera system transiting part of the GI lumen according to one embodiment of the present invention.
Figure 3:
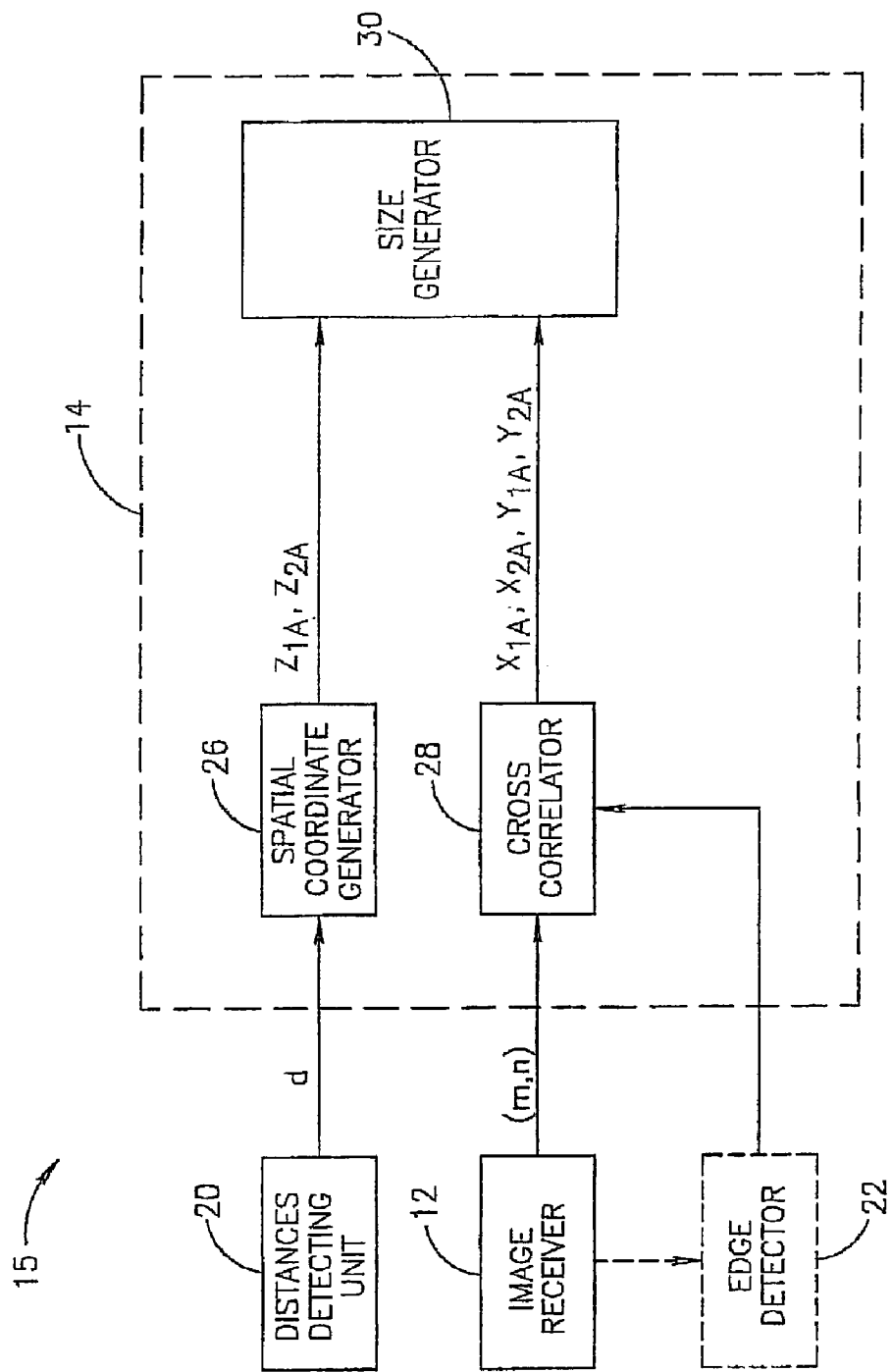
FIG. 3 is a block diagram illustration of a system according to one embodiment of the present invention.

Reference is now made to FIGS. 2 and 3, which illustrate a video capsule 40 inside the gut approaching two objects, and a system 15 for determining the size of one of the objects, according to one embodiment of the present invention. In one embodiment, system 15 is located in an external processing and display system, such as a personal computer or workstation, including conventional equipment and software such as a microprocessor or CPU, a memory, storage, etc. For example, system 15 may be located in a display system described in embodiments of U.S. Pat. No. 5,604,531 and/or International Application Publication No WO0165995 published Sep. 13, 2001. In alternate embodiments, all or part of system 15 or the functionality of system 15 may be located in another location or in other equipment. For example, some functionality may be in capsule 40.

In FIG. 2, video capsule 40 is shown approaching a first object 401 and a second object 402, in GI lumen 403. Using two, typically, but not necessarily, consecutive images captured by capsule 40 and the known speed of capsule 40, size analysis based on three dimensional representations of objects 401 and 402 can be done, as will be discussed with regard to FIG. 5 below.

Figure 4:
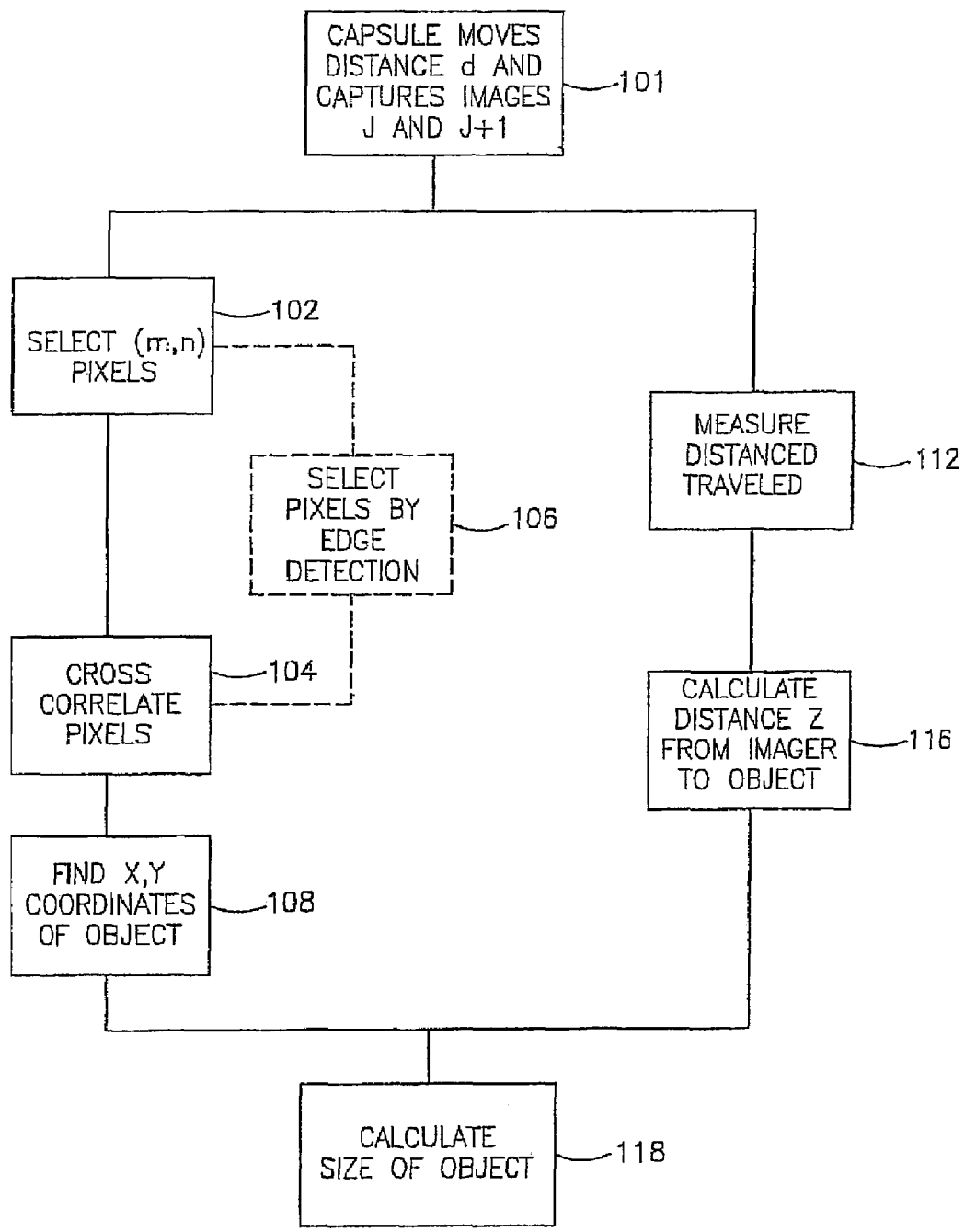
FIG. 4 is a flow chart illustration of the method used by the system shown in FIG. 3, according to an embodiment of the invention.

Referring to FIG. 3, system 15 includes, for example, a distance-detecting unit 20, an image receiver 12 and a processor 14. Processor 14 includes, for example, a spatial coordinate generator 26, a cross correlation 28 and a size generator 30. In one embodiment, distance-detecting unit 20 is a position detector. In one embodiment, distance-detecting unit 20 obtains a distance measurement d by measuring and integrating a velocity, as will be described hereinbelow. Processor 14 may include, for example, a standard PC accelerator board, high performance PC, multiprocessor PC or any other serial or parallel high performance processing machine, and appropriate software. Optionally, system 15 may include, for example, an edge detector 22. The functionality of one or more of distance-detecting unit 20, spatial coordinate generator 26, cross correlator 28, edge detector 22 and/or size generator 30 may be contained within or controlled by processor 14. Any suitable edge detector or edge detection capability used in conventional image analysis can be used, such edge detection capability using the following sliding window filter:

Reference is now made to FIG. 4 which is a flow chart diagram illustrating a $$\begin{bmatrix} -1 & 0 & -1 \\ 0 & 4 & 0 \\ -1 & 0 & -1 \end{bmatrix}$$

general method for generating size measurements from two-dimensional images according to one embodiment of the present invention. Steps of FIG. 4 may be accomplished using, for example, the system 15 of FIG. 3. In another embodiment, the embodiments of the methods described herein may be practiced using equipment or devices of other configurations. First, imager 46 within a moving in vivo video camera system such as the one described in FIG. 1) captures (step 101) images periodically, such as every 100-1000 ms. In one embodiment, the images are captured every 500 ms. Image data is transmitted to image receiver 12 (FIG. 1). Data processor 14 divides received images into a grid of pixels, and selects (step 102) pixels for analysis. As in other imaging applications, the number of pixels determines the resolution of the image. For purposes of this discussion, the images are divided into m×n pixels.

In one embodiment, a user may choose which object or objects are to be tracked for size analysis. For example, a user may select an object, objects, or region being displayed in a moving or still image on a monitor using, for example, a pointing device such as a mouse. According to one embodiment an object is selected in a manner similar to selecting an object during ultrasound procedures. In another embodiment the system may automatically chose an object(s) or region for size analysis. In one embodiment, the calculations are performed on a workstation with stored data, and a user is able to move forward and backwards through a moving image and see or request size information for the various objects displayed during the portion viewed. In another embodiment, size analysis may be performed in real time. Size information may be, for example, stored and/or displayed. Other object or region selecting methods may be used.

Next, cross correlator 28 calculates (step 104) an xy cross correlation function between the intensities $I_j$ and $I_{j+n}$ of image j and image j+n, thereby identifying corresponding pixels in images j and j+n. The value n is typically, but not necessarily, 1. Henceforth, the second frame will be designated as j+1, with the understanding that n can also be greater than 1.

The correlation can be done for each of the m×n pixels created in images j, and j+1. However, in another embodiment, edge detector 22 selects (step 106) pixels for cross correlation, thereby selecting an object. In one embodiment, only pixels whose edges exceed a certain predetermined threshold value are selected for correlation. Other suitable methods for image processing may be used.

While the cross correlation can be done on a pixel by pixel basis, more typically, it is performed on parts of the image, such as sets of 8×8 pixels. The latter approach can be used to minimize computation time.

In one typical cross correlation function, the cross correlation coefficient $C_{xy}$ is given by:

$$C_{xy} = \Sigma\Sigma I_j(m,n) I_{j+1}(m+x, n+y)$$
$$\phantom{C_{xy} = } m \phantom{\Sigma} n$$

where $I_j(m,n)$ and $I_{j+1}(m,n)$ are the intensity values of pixel (m,n) in images j and j+1 respectively. The vector (x, y) can be considered the displacement vector from pixel (m,n) in going from pixel (m,n) to pixel (m+x, n+y). The maximum of the cross correlation function indicates the most probable location of correspondence between the pixels of images j and j+1. A suitable cross correlation function is included in Matlab, a standard mathematics package for computers; other functions may be used.

The results of the cross correlation may provide, for example, x and y coordinates for a specific point. If the cross correlation is performed for, for example, four edges of an object on images j and j+1, an entire two-dimensional set of spatial coordinates is obtained (step 108). Thus, for object A, $x_{1A}$, $x_{2A}$, $y_{1A}$ and $y_{2A}$ are known.

The determination of the z coordinates for object A is typically based on the distance traversed by imager 46 while it moves through the GI tract capturing images j and j+1. Typically, distance traveled is determined from data captured by a sensor which is typically located within the device containing the capsule 40; the sensor may alternately be external to the patient. In one embodiment, distance-measuring unit 20 measures the velocity of imager 46 using an accelerometer and an integrator.

The accelerometer may be, for example, the ADXL50 model from Analog Devices. It is readily evident that, in addition to an accelerometer, any sensor that can provide data to determine the velocity of the capsule could also be used. Such sensors include, but are not limited to, induction coils (as described in U.S. Pat. No. 4,431,005, incorporated herein by reference) and ultrasound transducers. For example, if an induction coil is located in the capsule and the patient is placed in a magnetic field, a current would be produced by the coil with a magnitude proportional to the velocity of the capsule. Similarly, ultrasound transducers, such as those used in conventional medical ultrasound devices, can be used as an external sensor to track the movement of the capsule and standard electronics could be used to convert the data to velocities. Other distance measurement systems and methods may be used.

In another embodiment, the change of position of the capsule while capturing two images can be used to determine the distance traveled by the capsule during the time interval between the images. Signals sent by a transmitter within the capsule and received by receivers outside the body can be used to locate the position of the capsule. One suitable system for determining capsule location is one described in Published U.S. Application Number US-2002-0173718-A1 assigned to the common assignee of the present application and incorporated herein by reference; other suitable location determining systems may be used.

In yet another embodiment, conventional image analysis techniques can be used to analyze the optical flow of the images. For example, on the basis of the smear pattern of the images, velocity or distance can be determined. Once the velocity is known, a, for example, integrator calculates (step 112) the distance traveled by imager 46 from the time of capture of image j to the time of capture of image j+1. This distance value is used in determining (step 116) the z coordinate of object A, as described in the methods provided as examples hereinbelow. Other methods may be used within the scope of the present invention.

One method described hereinbelow is adapted from a method discussed in *Machine Vision Theory, Algorithms, Practicalities*, E. R. Davies, Academic Press 1996, pp. 441-444, incorporated herein by reference. Davies describes how a camera, when moving along a baseline, sees a succession of images. Depth information can be obtained by analyzing the object features of two images.

In general, the discussion by Davies uses far-field approximations; he discusses systems where the distance traveled by a camera between images is far smaller than the distance to the object. That is a condition that typically does not apply to in vivo video camera systems imaging the GI tract. In vivo video camera systems typically move distances that are non-negligible in size when compared to the distances between the camera and objects being imaged. Because far field approximations are typically not valid for in vivo video camera systems, images of two objects may be required, where one object serves as a reference object.

Figure 5:
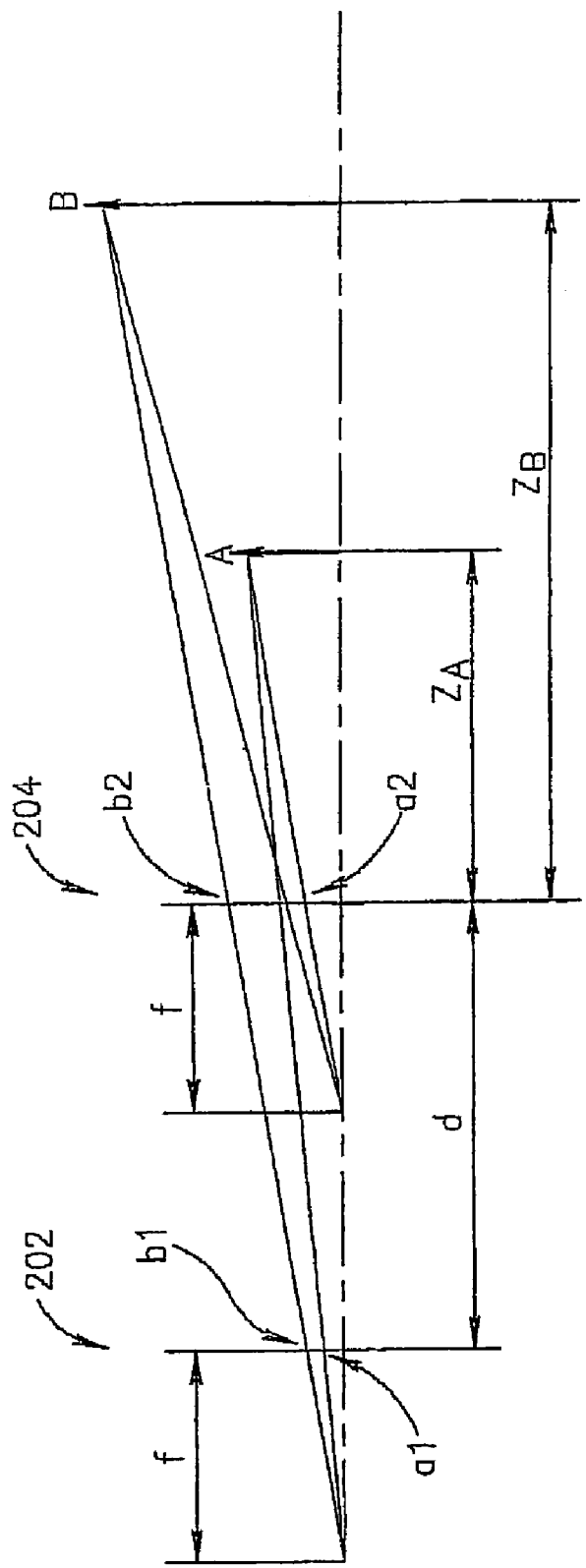
FIG. 5 is a schematic illustration showing how spatial coordinates are determined according to an embodiment of the present invention.

Reference is now made to FIG. 5, which shows a geometric illustration of the basis for calculating the z coordinate of a set of objects A and B (where set can include one item), according to one embodiment of the present invention. It should be noted that the z coordinate represents the distance from imager 46 to each of the objects, denoted $z_A$ and $z_B$ respectively.

As mentioned above, imager 46 typically moves a certain distance d from the capture of the first image 202 to the capture of the second image 204 (of course periods of little or no movement are possible). Thus, the distance between images 202 and 204 is distance d. In addition, there is a certain focal length f, which is the lens focal length. While in one embodiment focal length f is used in the derivation of the following equations, it is typically eventually eliminated and in such a case its value does not need to be known explicitly.

The projections of objects A and B on each of the images 202 and 204 in the y direction are shown in FIG. 5 and are denoted a1, b1, a2 and b2, respectively. These values are obtained from, for example, the pixel information stored in storage unit 19, and correspond to the n value of each m×n pixel. Thus, for example, a1 represents the X value of object A as it was acquired in time t1 ($X_{1A}$) and a2 represents the X value of object A as it was acquired in time t2 ($X_{2A}$). Accordingly, b1 represents the X value of object B as it was acquired in time t1 ($X_{1B}$) and b2 represents the X value of object B as it was acquired in time t2 ($X_{2B}$).

The actual values for a1, a2, b1, and b2 may be calculated by, for example, image processor 14 (step 108 of FIG. 4) from, for example, the size of the image sensor in imager 46 and image pixel data stored in storage unit 18. Thus, if the image sensor has a length L, and there are m pixels along the X axis, then an object whose length is p pixels will have an actual size of: L*P/m.

Using similar triangles, it can be shown that the following relationship exists:

$$Z_b(1-T_b) = Z_a(1-T_a) + d(T_b - T_a)$$

where $T_a$ and $T_b$ are defined as:

$$T_a = a_1/a_2$$

$$T_b = b_1/b_2$$

Thus, the z coordinate for object A as a function of the z coordinate for object B can be obtained. Spatial coordinate processor 26 calculates (step 116) the z values for two points on object A ($Z_{1A}$ and $z_{2A}$) corresponding to the two edges of object A. Accordingly, xyz spatial coordinates are known for object A. Size analyzer 30 then calculates (step 118) the size of object A by, for example, subtracting each of the axis coordinates from each other. Thus, $x_A = x_{2A} - x_{1A}$; $y_{2A} - y_{1A}$; and $z_A = z_{2A} - z_{1A}$, resulting in values for length, width and height, respectively, of object A.

Other formulas and methods of calculation can be used, falling within the scope of the present invention.

Alternatively, other methods can be used to calculate $z_A$, such as one based on the following exemplary relationships:

$$A/a_1 = (Z_A + d + f)/f$$

$$A/a_2 = (Z_A + f)/f$$

From those two equations the following can be calculated:

$$A*f = (Z_A + d + f)/a_1 + (Z_A + f)*a_2$$

Leading to $$Z_A*a_1 - Z_A*a_2 = f*a_2 - (d+f)*a_1 = f*(a_2 - a_1) - d*a_1$$

Finally, $$Z_A = d*a_1/(a_2 - a_1) - f$$

Thus, if the focal length of the camera is known, only one object is needed for calculation. The size of the object may calculated, for example, as described above.

Image processor 14 may send any selected size-data to image monitor 18 for display. Such size data may be displayed along with, for example, image or moving image data on image monitor 18. Various methods of displaying the size data may be used.

The procedure described hereinabove can be performed as a post-processing step, or, with adequate computational capability, it can be done in real time, allowing the user to choose specific images for processing.

It should be evident that while FIG. 5 shows a one-dimensional object, (e.g. a line), here positioned along the X-axis, symmetry considerations can be used in an analogous manner to obtain the Y coordinate, where the Y-axis is perpendicular to the plane of the paper.

For the above described methods, other steps or series of steps may be used. Furthermore, with the various formulas and methods of calculation presented above, other formulas and methods of calculation can be used, falling within the scope of the present invention. While specific formulas and dimensions are presented, other formulas, or variants of the formulas presented, and other dimensions, may be used.

It will be appreciated by persons skilled in the art that the present invention is not limited to what has been particularly shown and described hereinabove. Rather the scope of the present invention is defined only by the claims that follow:

What is claimed is:

1. A method for calculating a size of an object in vivo using images acquired by an imager, the method comprising:
   determining a distance traveled by said imager during capture of two of said images;
   calculating relative spatial coordinates of a set of objects within said images using said distance; and
   calculating the size of one of the set of objects from said spatial coordinates;
   wherein the above steps are performed by a processor.

2. The method according to claim 1 wherein said distance traveled is non-negligible as compared to a distance between said imager and said objects.

3. The method according to claim 1 wherein the imager is included within an endoscope.

4. The method according to claim 1 wherein the imager is included within a swallowable capsule.

5. The method according to claim 1 comprising determining the position of the imager.

6. The method according to claim 1 comprising determining the velocity of the imager.

7. The method according to claim 1 comprising determining an optical flow of the images.

8. The method according to claim 1 comprising determining the distance traveled by analyzing the images.

9. The method according to claim 1 wherein the object is in a gastrointestinal tract.

10. A swallowable capsule comprising:
   an image sensor capable of obtaining images from within the gastrointestinal tract;
   a distance-detecting sensor capable of generating data for determining a distance traveled by said capsule during reception of at least two of said images, wherein said data may be used by a processor for generating spatial coordinates of at least one object found within said two images and for converting said spatial coordinates into a size calculation of said at least one object.

11. The capsule according to claim 10 where said distance-detecting sensor includes an induction coil.

12. The capsule according to claim 10 wherein said distance-detecting sensor includes a velocity sensor.

13. The capsule according to claim 10 wherein distance-detecting sensor includes an imager.

* * * * *